(12) United States Patent
Murthy et al.

(10) Patent No.: US 8,198,434 B2
(45) Date of Patent: Jun. 12, 2012

(54) PROCESS FOR PREPARING CEFSULODIN SODIUM

(75) Inventors: Yerramilli V. S. N. Murthy, Apex, NC (US); Edward Obare, Portland, ME (US); Hengguang Li, Morrisville, NC (US)

(73) Assignee: IDEXX Laboratories, Inc., Westbrook, ME (US)

(*) Notice: Subject to any disclaimer, the term of this patent is extended or adjusted under 35 U.S.C. 154(b) by 251 days.

(21) Appl. No.: 12/435,462

(22) Filed: May 5, 2009

(65) Prior Publication Data

US 2010/0113768 A1 May 6, 2010

Related U.S. Application Data

(60) Provisional application No. 61/051,153, filed on May 7, 2008.

(51) Int. Cl.
*C07D 501/54* (2006.01)
(52) U.S. Cl. ...................................... 540/224
(58) Field of Classification Search ............... 540/224
See application file for complete search history.

(56) References Cited

U.S. PATENT DOCUMENTS

| | | | |
|---|---|---|---|
| 3,579,514 A * | 5/1971 | McGregor | 540/225 |
| 3,646,024 A * | 2/1972 | Holdrege | 540/225 |
| 3,646,025 A * | 2/1972 | Crast, Jr. | 540/224 |
| 3,792,047 A * | 2/1974 | Arkley et al. | 540/225 |
| 3,954,826 A | 5/1976 | Sugimoto et al. | |
| 3,988,327 A | 10/1976 | Ishiguro et al. | |
| 4,026,940 A | 5/1977 | Sugimoto et al. | |
| 4,029,656 A | 6/1977 | Ishiguro et al. | |
| 4,060,687 A * | 11/1977 | Christensen et al. | 540/227 |
| 4,065,619 A | 12/1977 | Morimoto et al. | |
| 4,144,248 A | 3/1979 | Tsuchibashi et al. | |
| 4,148,817 A | 4/1979 | Wright et al. | |
| 4,160,830 A | 7/1979 | Morimoto et al. | |
| 4,169,947 A * | 10/1979 | Treuner et al. | 540/227 |
| 4,172,197 A * | 10/1979 | Shibuya et al. | 540/227 |
| 4,224,441 A * | 9/1980 | Tsushima et al. | 540/215 |
| 4,245,088 A | 1/1981 | Tsushima et al. | |
| 4,317,907 A | 3/1982 | Saikawa et al. | |
| 4,414,328 A | 11/1983 | Imanaka et al. | |
| 4,608,373 A * | 8/1986 | Shibanuma et al. | 514/202 |
| 4,709,023 A * | 11/1987 | Angerbauer | 540/224 |
| 4,803,267 A * | 2/1989 | Smith | 540/224 |
| 4,925,789 A | 5/1990 | Eldberg | |
| 4,980,464 A | 12/1990 | Naito et al. | |
| 5,144,027 A | 9/1992 | Sadaki et al. | |
| 2003/0149014 A1* | 8/2003 | Nishitani et al. | 514/203 |

FOREIGN PATENT DOCUMENTS

JP 59 227822 12/1984

OTHER PUBLICATIONS

Cefsulodin Sodium—Product Data Sheet <http://www.toku-e.com/Upload/Products/PDS/20110329006764.pdf> downloaded from the internet Jul. 18, 2011.*
"Cefsulodin & Related Products from Molcan" <http://www.molcan.com/cefsulodin.htm> downloaded from the internet Jul. 18, 2011.*
"Cefsulodin (C22H20N4O8S2)—Chembase—Chemical Compounds Database" <http://chembase.com/cbid_44097.htm> downloaded from the internet Jul. 18, 2011.*
"Cefsulodin sodium salt hydrate | Sigma-Aldrich.com" <http://www.sigmaaldrich.com/catalog/ProductDetail.do?D7=0&N5=SEARCH_CONCAT_PNO%7CBRAND_KEY&N4=C8145%7CSIGMA&N25=0&QS=ON&F=SPEC> downloaded from the internet Jul. 18, 2011.*
"ChemNet Cefsulodin Sodium" <http://www.chemnet.com/ChinaSuppliers/33581/Cefsulodin-Sodium--1089806.html> downloaded from the internet Jul. 18, 2011.*
"Cefsulodin—Compound Summary (CID 5284530)" <http://pubchem.ncbi.nlm.nih.gov/summary/summary.cgi?cid=5284530>downloaded from the internet Jul. 18, 2011.*
"CAS No. 62587-73-9 Suppliers and pirces" <http://www.weiku.com/chemicals/62587-73-9.html> downloaded from the internet Jul. 18, 2011.*
Nakamachi, Chem. Pharm Bull 28, 3457 (1978).*
Zhong Yu, Huaxi Yaoxue Zazhi (2007), 22(2), 182-183.*
Translation of Zhong Yu, Huaxi Yaoxue Zazhi (2007), 22(2), 182-183.*
Office communication in the Chinese No. 200910141998.6 application dated Jan. 6, 2011.
Xue Zhe et al., "The progress of study on cefsulodin sodium" Practical Clinical Medicine, 2007, vol. 8, No. 11, p. 137-138.
Hiroaki Nomura et al., Journal of Medicinal Chemistry, vol. 17, No. 12, p. 1312-1315, 1974.
H. Nomura et al., J. Med. Chem., (1974), vol. 15, No. 12, p. 1312.
H. Nomura et al., Heterocycles (1974), p. 67-72.
S. Morito et al., J. Med. Chem., (1972), vol. 15, No. 11, p. 1108.
Office communication in the EP 09006167.2 application dated Jun. 30, 2009.
J. M. Aizpurua and C. Palomo, *Reagents and Synthetic Methods, 31, Silylations with N-Trimethylsilyl-2-oxazolidinone (TMSO)*, Can. J. Chem., vol. 62, 1984 336-340.
JP 53124608, 1978 (English translation of Examples 21 and 22).
Print out from the Wikepedia website for cefsulodin ( http://en.wikipedia.org/wiki/Cefsulodin), Feb. 16, 2012. Print out from the Sigma Aldrich website for cefsulodin sodium salt hydrate at (https://www.sigmaaldrich.com/etc/medialib/docs/Sigma/Product_Information_Sheet/c8145pis.Par.0001.File.tmp/c8145pis.pdf), Feb. 16, 2012.
"Certificate of Analysis" for cefsulodin sodium provided by A.G. Scientific Inc. at their website (http://www.agscientific.com/apoptosis/antibiotics/cefsulodin-sodium-salt.html), Feb. 16, 2012.

* cited by examiner

*Primary Examiner* — Mark Berch
(74) *Attorney, Agent, or Firm* — Haynes and Boone, LLP (57) ABSTRACT

The invention is directed to an improved process for preparing cefsulodin sodium. The process involves: (i) dissolving cefsulodin in a solvent comprising an organic solvent to provide a solution of cefsulodin, (ii) adding about 1 equivalent of a sodium salt of a base to the solution of cefsulodin to provide a solution of cefsulodin sodium, and (iii) separating the cefsulodin sodium from the solution of cefsulodin sodium.

41 Claims, 3 Drawing Sheets

PROCESS FOR PREPARING CEFSULODIN SODIUM

CROSS-REFERENCES TO RELATED APPLICATIONS

This application claims the benefit of U.S. Provisional Application Ser. No. 61/051,153, tiled May 7, 2008, the contents of which are expressly incorporated herein.

STATEMENT AS TO RIGHTS TO INVENTIONS MADE UNDER FEDERALLY SPONSORED RESEARCH AND DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The invention is directed to a method for making cefsulodin sodium. The cefsulodin prepared by the method of the invention has improved stability and better purity compared to cefsulodin sodium made by the typical process for making cefsulodin sodium.

Cefsulodin is a cephalosporin antibiotic containing the β-lactam structure. The following patents and publications relate to β-lactam antibiotics, including cefsulodin: H. Nomura et al., J. Med. Chem., (1974), vol. 15, no. 12, p. 1312; H. Nomura et al., Heterocycles (1974), p. 67-72; S. Morito et al., 3. Med. Chem., (1972), vol. 15, no. 11, p. 1108; U.S. Pat. Nos. 4,026,940; 3,954,826; 4,160,830; 4,029,656; 3,988,327; 4,065,619; 4,144,248; 4,414,328; 4,172,197; 5,144,027; 4,980,464; 4,148,817; 4,317,907; 4,925,789; and 5,144,027.

Citation of any reference in this section of this application is not to be construed that such reference is prior art to the present application.

BRIEF SUMMARY OF THE INVENTION

The invention is directed to a process for making cefsulodin sodium comprising:
(i) dissolving cefsulodin in a solvent comprising an organic solvent to provide a solution of cefsulodin,
(ii) adding about 1 equivalent of a sodium salt of a base to the solution of cefsulodin to provide a solution of cefsulodin sodium, and
(iii) separating the cefsulodin sodium from the solution of cefsulodin sodium.

In one embodiment, the invention is directed to a process for making cefsulodin sodium comprising:
(i) dissolving cefsulodin in dimethylformamide or a mixture of dimethylformamide and water to provide a solution of cefsulodin,
(ii) adding about 1 equivalent of a sodium salt of a base to the solution of cefsulodin to provide a solution of cefsulodin sodium, and
(iii) separating the cefsulodin sodium from the solution of cefsulodin sodium.

In one embodiment, the invention is directed to a process for making cefsulodin sodium comprising:
(i) dissolving cefsulodin in ethanol or a mixture of ethanol and water to provide a solution of cefsulodin,
(ii) adding about 1 equivalent of a sodium salt of a base to the solution of cefsulodin to provide a solution of cefsulodin sodium, and
(iii) separating the cefsulodin sodium from the solution of cefsulodin sodium.

The separated cefsulodin sodium is optionally dried to a water content ranging from about 2.0 to 4.5% by weight. In one embodiment, the cefsulodin sodium is dried to a water content ranging from about 3.0 to 4.0% by weight. In one embodiment, the cefsulodin sodium is dried to a water content ranging from about 3.5 to 4.0% by weight.

In one embodiment, the sodium cefsulodin are needle-shaped crystals.

In one embodiment, the sodium cefsulodin are spherical-shaped crystals.

DETAILED DESCRIPTION OF THE INVENTION

The invention is directed to a process for making cefsulodin sodium comprising:
(i) dissolving cefsulodin in a solvent comprising an organic solvent to provide a solution of cefsulodin,
(ii) adding about 1 equivalent of a sodium salt of a base to the solution of cefsulodin to provide a solution of cefsulodin sodium, and
(iii) separating the cefsulodin sodium from the solution of cefsulodin sodium.

The phrase "cefsulodin sodium," as used herein, means the sodium salt of cefsulodin and includes the monosodium salt of cefsulodin, the disodium salt of cefsulodin, and mixtures thereof.

Cefsulodin has the structure

The monosodium salt of cefsulodin has the structure

It will be appreciated, however, that the monosodium salt of cefsulodin will also include some of the compound wherein the carboxylic acid group of cefsulodin is deprotonated rather than the sulfonic acid group of cefsulodin. The sulfonic acid group is preferentially deprotonated because sulfonic acids are more acidic than carboxylic acids. Thus, the predominate species present in the monosodium salt of cefsulodin has the structure depicted above, i.e., the structure wherein the sulfonic acid group is deprotonated.

The disodium salt of cefsulodin has the structure

Preferably, the cefsulodin sodium prepared by the method of the invention is predominately the mono sodium salt of cefsulodin.

In one embodiment, the solvent comprising an organic solvent further comprises water.

In one embodiment, the solvent comprising an organic solvent is substantially free of water.

In one embodiment, the solvent comprising an organic solvent is dimethylformamide.

In one embodiment the solvent comprising an organic solvent is dimethylformamide substantially free of other organic solvents.

In one embodiment, the solvent comprising an organic solvent is a mixture of dimethylformamide and water.

In one embodiment, the solvent comprising an organic solvent is dimethylformamide substantially free of water.

In one embodiment, the solvent comprising an organic solvent is ethanol.

In one embodiment the solvent comprising an organic solvent is ethanol substantially free of other organic solvents.

In one embodiment, the solvent comprising an organic solvent is a mixture of ethanol and water.

In one embodiment, the solvent comprising an organic solvent is ethanol substantially free of water.

The phrase "substantially free of," as used herein, means less than about 2 percent by weight, preferably less than about 1 percent by weight, more preferably less than about 0.5 percent by weight, and most preferably less than about 0.2 percent by weight. For example, the phrase "dimethylformamide substantially free of water" means that the amount of water in the dimethylformamide is less than about 2 percent by weight of the combined amount of dimethylformamide and water, preferably less than about 1 percent by weight of the combined amount of dimethylformamide and water, more preferably less than about 0.5 percent by weight of the combined amount of dimethylformamide and water, and most preferably less than about 0.2 percent by weight of the combined amount of dimethylformamide and water.

The concentration of cefsulodin in the solvent comprising an organic solvent is not important, however, it is preferable that at least 90% of the cefsulodin is dissolved in the solvent comprising an organic solvent. In one embodiment, at least 95% of the cefsulodin is dissolved in the solvent comprising an organic solvent. In one embodiment, at least 99% of the cefsulodin is dissolved in the solvent comprising an organic solvent. In one embodiment, all of the cefsulodin is dissolved in the solvent comprising an organic solvent.

The term "solution," as used herein, has its art recognized meaning, i.e., a uniformly dispersed mixture at the molecular or ionic level of one or more substances (solute) in one or more other liquid substances (solvent).

The term "suspension," as used herein, has its art recognized meaning, i.e., solid particles that are evenly dispersed in a solvent.

The sodium salt of a base can be any sodium salt of a base that is capable of deprotonating the cefsulodin. For example, the sodium salt of a base can be sodium hydroxide. However, the sodium salt of a base is preferably a sodium salt of a carboxylate anion. Suitable carboxylate salts include, but are not limited to, acetate, propionate, and butyrate salts. Sodium acetate is preferred.

Typically, the sodium salt of a base is added to the solution of cefsulodin as a solution of the sodium salt of the base in a solvent. Any solvent that is capable of dissolving the sodium salt of the base can be used in the process of the invention if the solvent is miscible with the solvent comprising an organic solvent and, when added to the solvent comprising an organic solvent, does not result in cefsulodin or the sodium salt of the base precipitating from the resulting mixture.

In one embodiment, water is the solvent that is capable of dissolving the sodium salt of the base.

In one embodiment, water is the solvent that is capable of dissolving the sodium salt of the base and the solvent comprising an organic solvent is dimethylformamide or a mixture of dimethylformamide and water.

In one embodiment, water is the solvent that is capable of dissolving the sodium salt of the base and the solvent comprising an organic solvent is ethanol or a mixture of ethanol and water.

The phrase "about," as used herein means, ±20%. Accordingly, the phrase "about 1 equivalent of a sodium salt of a base relative to the cefsulodin," means 1±0.2 equivalents of the sodium salt of a base relative to the cefsulodin. In one embodiment, 1±0.1 equivalents of the sodium salt of a base relative to the cefsulodin is used in the process. In one embodiment, 1±0.05 equivalents of the sodium salt of a base relative to the cefsulodin is used in the process. In one embodiment, 1±0.02 equivalents of the sodium salt of a base relative to the cefsulodin is used in the process.

The process can be conducted at any suitable temperature for carrying out the reaction process. The process, for example, can be conducted at room temperature, i.e., about 25° C.

The cefsulodin sodium can be separated from the solution of cefsulodin sodium by any means known in the art. Suitable methods include, but are not limited to removing solvent from the solution of cefsulodin sodium by distillation or by adding an anti-solvent to the solution of cefsulodin sodium to precipitate the cefsulodin sodium and collecting the precipitated cefsulodin sodium (for example, by filtering or centrifugation). The collected cefsulodin sodium can optionally be washed with a solvent and/or dried.

In one embodiment, the solvent comprising an organic solvent is dimethylformamide or a mixture of dimethylformamide and water, the sodium salt of a base is sodium acetate, and the cefsulodin sodium is separated from the solution of cefsulodin sodium by adding water as an anti-solvent to precipitate the cefsulodin sodium.

Accordingly, in one embodiment, the process for making cefsulodin sodium comprises:

(i) dissolving cefsulodin in dimethylformamide or a mixture of dimethylformamide and water to provide a solution of cefsulodin, (ii) adding about 1 equivalent of sodium acetate to the solution of cefsulodin to provide a solution of cefsulodin sodium, and (iii) separating the cefsulodin sodium from the solution of cefsulodin sodium.

In one embodiment, the sodium acetate is added as a solution of sodium acetate. In one embodiment, the sodium acetate is added as an aqueous solution of sodium acetate. In one embodiment, the cefsulodin sodium is separated from the solution of cefsulodin sodium by adding water as an anti-solvent to precipitate the cefsulodin sodium.

In one embodiment, the solvent comprising an organic solvent is a mixture of ethanol and water, the sodium salt of a base is sodium acetate, and the cefsulodin sodium is separated from the solution of cefsulodin sodium by adding additional ethanol as an anti-solvent to precipitate the cefsulodin sodium.

Accordingly, in one embodiment, the process for making cefsulodin sodium comprises:

(iv) dissolving cefsulodin in ethanol or a mixture of ethanol and water to provide a solution of cefsulodin,

(v) adding about 1 equivalent of sodium acetate to the solution of cefsulodin to provide a solution of cefsulodin sodium, and (vi) separating the cefsulodin sodium from the solution of cefsulodin sodium.

In one embodiment, the sodium acetate is added as a solution of sodium acetate. In one embodiment, the sodium acetate is added as an aqueous solution of sodium acetate. In one embodiment, the cefsulodin sodium is separated from the mixture of ethanol and water by adding ethanol as an anti-solvent to precipitate the cefsulodin sodium.

Typically, the sodium salt of a base is added to the solution of cefsulodin in an amount sufficient to provide a pH that ranges from about 3.8 to about 4.4, preferable about 4.0 to about 4.3.

The cefsulodin used in the process of the invention can be prepared by any method known to those skilled in the art. An illustrative method is provided below:

-continued

The cefsulodin sodium prepared by the process of the invention is superior to cefsulodin sodium prepared by the typical manufacturing processes for making cefsulodin sodium, which involves suspending cefsulodin in water (cefsulodin is insoluble in water) and adding sodium hydroxide to the aqueous suspension. For example, the cefsulodin sodium obtained by the process of the invention has improved stability compared to cefsulodin sodium made by the typical manufacturing processes (i. e., adding sodium hydroxide to an aqueous suspension of cefsulodin).

By way of example, cefsulodin sodium prepared by the typical manufacturing process, having a purity determined by high pressure liquid chromatography (HPLC) of about 95%, after storage at about room temperature for 29 days showed a purity of 80.4% and after 56 days a purity of 76.7%. In contrast, cefsulodin sodium prepared by the process of the invention is expected to show significantly better stability.

In one embodiment, the process further involves drying the cefsulodin sodium to a water content ranging from about 2.0 to 4.5% by weight. Drying the cefsulodin sodium to a water content within this range further improves the stability. In one embodiment, the cefsulodin sodium is dried to a water content ranging from about 3.0 to 4.0% by weight. In one embodiment, the cefsulodin sodium is dried to a water content ranging from about 3.5 to 4.0% by weight. It has been unexpectedly discovered that cefsulodin sodium having a water content within this range exhibits superior stability compared to cefsulodin sodium having a water content falling outside of this range, (i.e., a higher water content or a lower water content).

The cefsulodin sodium can be dried by any method known to those skilled in the art, such as, but not limited to, drying under reduced pressure and/or drying under heat. It is preferable that the cefsulodin sodium be in the form of a powder when it is dried because cefsulodin sodium that has a highly granular texture or lumps may entrap water and make its removal difficult.

The water content of the cefsulodin sodium can be determined by any method known to those skilled in the art such as, but not limited to, weight loss on drying or, preferably, Karl-Fischer titration.

Without wishing to be bound by theory it is believed that cefsulodin sodium prepared by the method of the invention has improved stability compared to cefsulodin sodium prepared by the typical manufacturing process because the cefsulodin sodium prepared by the method of the invention has lower amounts of the disodium salt of cefsulodin compared to cefsulodin sodium prepared by the typical manufacturing process. Without wishing to be bound by theory, it is believed that the disodium salt of cefsulodin is more prone to degradation than the monosodium salt of cefsulodin. A possible degradation pathway for the disodium salt of cefsulodin (less likely with the monosodium salt of cefsulodin) is depicted below:

Without wishing to be bound by theory, it is believed that the cefsulodin sodium prepared by the process of the invention has a lower amount of disodium cefsulodin than cefsulodin sodium prepared by the typical manufacturing process because the typical manufacturing process employs a suspension of cefsulodin and the process of the invention employs a solution of cefsulodin. As discussed above, the typical process for making cefsulodin sodium involves adding sodium hydroxide to a suspension of cefsulodin. Cefsulodin is insoluble in water. The monosodium cefsulodin that is formed when cefsulodin is deprotonated by the sodium hydroxide, however, is more soluble in water that cefsulodin. Deprotonating cefsulodin with sodium hydroxide, however, is a slow process because the sodium hydroxide is dissolved in the water and the insoluble cefsulodin is not dissolved. Therefore, the sodium hydroxide, which is in solution, reacts readily with the monosodium salt once it forms, which is also in solution, to form the disodium salt of cefsulodin and reacts less readily with the cefsulodin that is not in solution. In contrast, the method of the invention uses a solution of cefsulodin in an organic solvent. Therefore, when the base (for example, sodium hydroxide) is added to the solution of cefsulodin, the preferred reaction is for the base to simply react with the cefsulodin (because both are in solution) to simply form the monosodium salt of cefsulodin. The process of the invention favors formation of the monosodium salt of cefsulodin and minimizes formation of the disodium salt of cefsulodin.

Another advantage of the process of the invention is that the resulting cefsulodin sodium is of higher purity than cefsulodin sodium obtained by the typical manufacturing process. Without wishing to be bound by theory, it is believed that the improved purity of the cefsulodin is because the typical manufacturing process uses sodium hydroxide in water and cefsulodin is unstable in water under basic conditions. Without wishing to be bound by theory, it is believed that the cefsulodin sodium degrades in water under basic conditions by the following pathway:

Although the degradation pathway depicted above shows hydroxide as a nucleophile to displace the pyridinium group of cefsulodin sodium, it will be appreciated that water can also act as the nucleophile.

The process of the invention minimizes this degradation pathway. In particular, using dimethylformamide as the solvent minimizes this degradation pathway. Similarly, using a weaker base than hydroxide (which will be less nucleophilic than hydroxide), in particular carboxylate anions, further minimizes this degradation pathway. Using dimethylformamide as the solvent and a carboxylate anion as the sodium salt of a base, in particular sodium acetate, is particularly advantageous.

The process of the invention, being a process that occurs in solution, occurs more quickly than the typical manufacturing process and, therefore, provides less time for degradation reactions to take place and also is less time consuming.

The invention further relates to cefsulodin made by the process of the invention.

In one embodiment, the cefsulodin sodium made by the process of the invention contains less than about 20% of the disodium salt of cefsulodin. In one embodiment, the cefsulodin sodium made by the process of the invention contains less than about 15% of the disodium salt of cefsulodin. In one embodiment, the cefsulodin sodium made by the process of the invention contains less than about 10% of the disodium salt of cefsulodin. In one embodiment, the cefsulodin sodium made by the process of the invention contains less than about 5% of the disodium salt of cefsulodin. In one embodiment, the cefsulodin sodium made by the process of the invention contains less than about 2% of the disodium salt of cefsulodin. The amount of the disodium salt of cefsulodin can be quantitatively determined using atomic absorption spectroscopy to determine the amount of sodium in a cefsulodin sodium sample.

The cefsulodin used in the process of the invention is preferably crystallized from dimethylformamide, optionally in combination with water. Without wishing to be bound by theory, it is believed that using dimethylformamide to crystallize cefsulodin provides cefsulodin of a purity that is better than can be obtained using other solvents. Thus, using cefsulodin crystallized from dimethylformamide provides cefsulodin sodium of higher purity that can be obtained from cefsulodin that has not been crystallized or has been crystallized from a solvent other than dimethylformamide.

It has also been discovered that cefsulodin sodium made by the process of the invention can exist in two crystalline forms, i.e., polymorphs. Specifically, the cefsulodin sodium can be spherical-shaped crystals or needle-shaped crystals. The crystalline forms can be distinguished from each other and from other solid state forms by their appearance under a microscope or by their powder X-ray diffraction (PXRD) pattern. Other methods well known to those skilled in the art for characterizing solid state forms can also be used to determine whether the cefsulodin sodium crystals are needle-shaped or spherical-shaped. These methods include, but are not limited to, solid state NMR, solid state IR, and differential scanning calorimetry (DSC).

Figure 1:
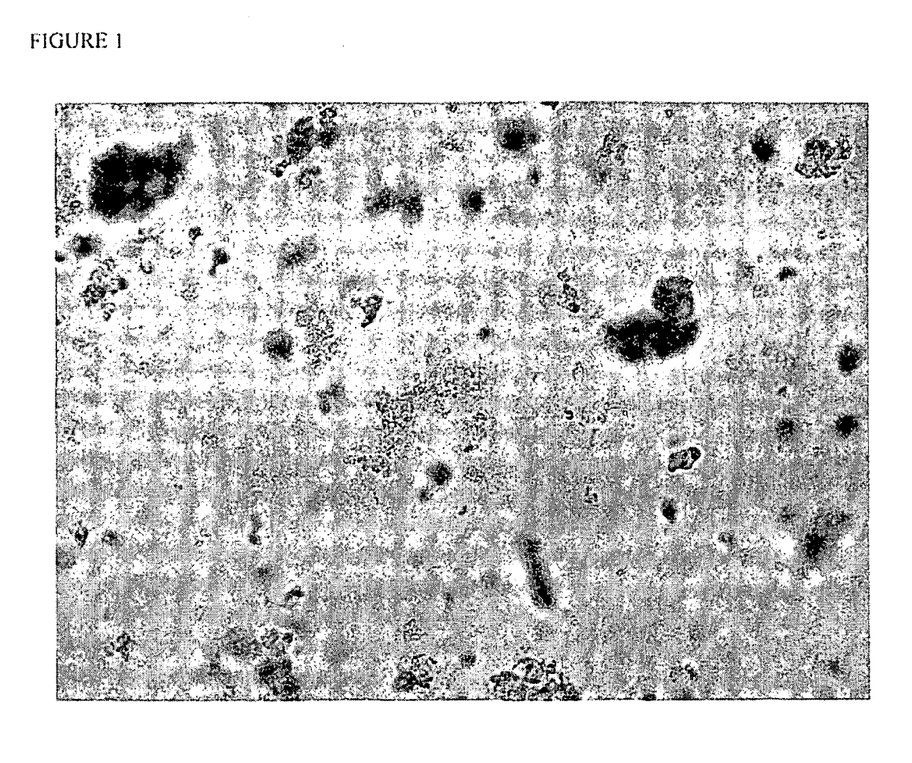
FIG. 1 illustrates the appearance of spherical-shaped crystals made by the process of the invention under a microscope.

Spherical-shaped cefsulodin sodium is obtained by the process of the invention by using a polar aprotic solvent as the organic solvent, optionally in combination with water. Suitable polar aprotic solvents include, but are not limited to, dimethylformamide and dimethyl sulfoxide. Preferably, the organic solvent is dimethylformamide. For example, spherical-shaped cefsulodin sodium can be obtained by the process of the invention using dimethylformamide-water as the solvent and precipitating the cefsulodin sodium, such as illustrated in Example 4. FIG. 1 illustrates the appearance of spherical-shaped crystals made by the process of the invention under a microscope.

Figure 2:
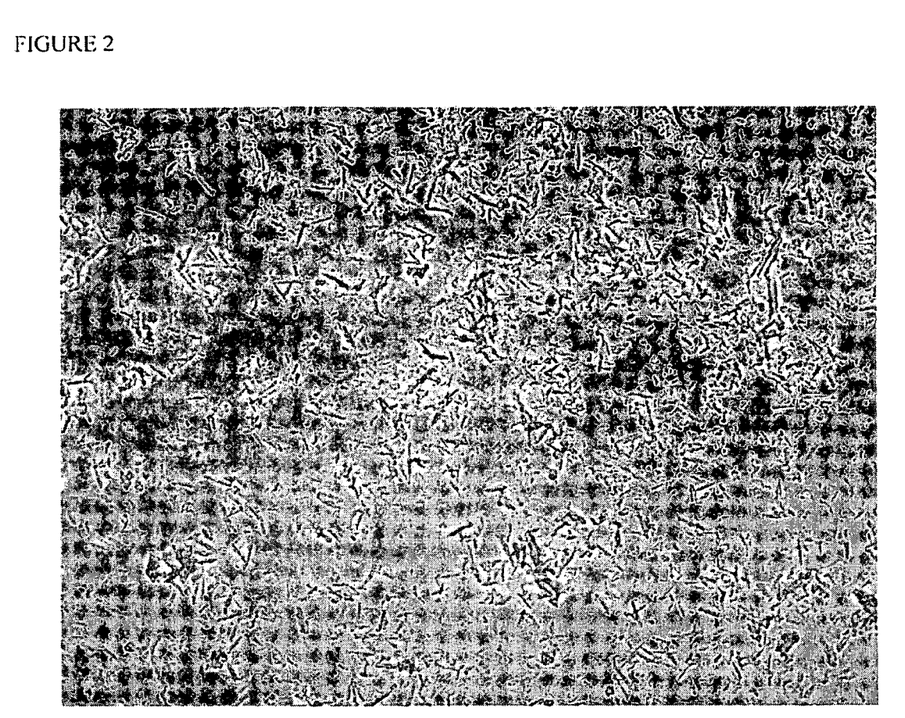
FIG. 2 illustrates the appearance of needle-shaped crystals made by the process of the invention under a microscope.

Needle-shaped cefsulodin sodium is obtained by the process of the invention using a $C_1$-$C_4$ alcohol as the organic solvent, optionally in combination with water. Preferably the organic solvent is ethanol. For example, needle-shaped cefsulodin sodium can be obtained by the process of the invention using ethanol-water as the solvent to dissolve the cefsulodin and precipitating the cefsulodin sodium using additional ethanol as an anti-solvent, such as illustrated in Example 2. FIG. 2 illustrates the appearance of needle-shaped crystals made by the process of the invention under a microscope.

Figure 3:
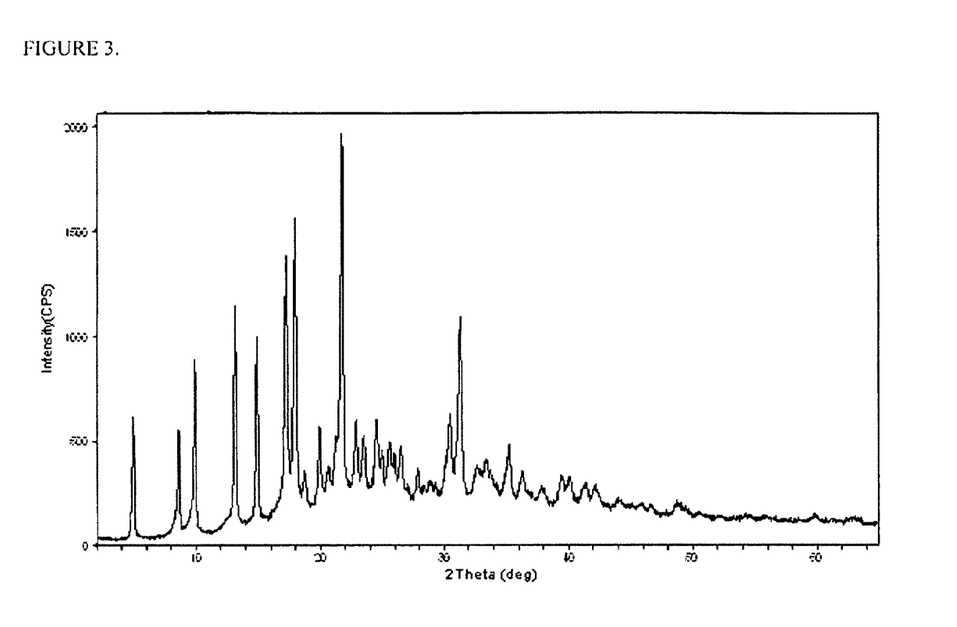
FIG. 3 is an powder X-ray diffraction pattern of needle-type crystals of cefsulodin sodium.

FIG. 3 illustrates the PXRD pattern of needle-type crystals. The PXRD pattern in FIG. 3 exhibits the following peaks at 2-theta (±2θ) values:

| 2-Theta Value | Intensity (height) |
|---|---|
| 4.8277 | 1501 |
| 8.4522 | 1138 |
| 9.7885 | 2043 |
| 13.0059 | 2767 |
| 14.7760 | 2302 |
| 17.0952 | 2890 |
| 17.8094 | 3428 |
| 18.5841 | 375 |
| 19.7905 | 935 |
| 21.4796 | 1237 |
| 12.4638 | 102 |
| 21.6032 | 4144 |
| 22.5895 | 446 |
| 22.7203 | 861 |
| 23.3437 | 704 |
| 24.3898 | 887 |
| 24.8302 | 463 |
| 25.4149 | 617 |
| 25.8237 | 439 |
| 26.3511 | 653 |
| 26.9057 | 150 |
| 27.7163 | 404 |
| 28.2576 | 169 |
| 28.7161 | 256 |
| 29.1511 | 169 |
| 30.2945 | 695 |
| 30.3625 | 567 |
| 31.6190 | 134 |
| 31.1577 | 1975 |
| 32.4721 | 151 |
| 32.7359 | 427 |
| 33.2521 | 275 |
| 33.6360 | 259 |
| 34.0630 | 129 |
| 34.8092 | 301 |
| 35.1010 | 618 |
| 36.1228 | 138 |
| 36.1641 | 374 |
| 36.8005 | 106 |
| 37.7661 | 233 |
| 39.3242 | 346 |
| 39.9500 | 315 |
| 40.2546 | 145 |
| 41.1600 | 256 |
| 41.9312 | 198 |
| 42.2255 | 121 |
| 43.8748 | 98 |
| 44.9512 | 187 |
| 45.6754 | 65 |
| 46.5176 | 92 |
| 48.5705 | 165 |
| 49.2793 | 98 |
| 50.3520 | 80 |
| 50.9900 | 40 |
| 51.9244 | 63 |
| 54.0962 | 82 |
| 55.7440 | 53 |
| 56.5077 | 42 |
| 57.9667 | 42 |
| 59.6413 | 88 |
| 61.0519 | 34 |
| 62.3503 | 41 |
| 62.9697 | 54 |
| 20.4663 | 309 |
| 21.1086 | 564 |

In one embodiment, the PXRD pattern of needle-type crystals exhibits the following characteristic peaks at 2-theta (±2θ) values 4.83, 8.45, 9.79, 13.00, 14.77, 17.09, 17.81, 21.48, 30.29, 31.16. In one embodiment, the PXRD pattern of needle-type crystals exhibits the following characteristic peaks at 2-theta (±2θ) values 4.83, 8.45, 9.79, 13.00, 14.77, 17.09, 17.81, 18.58, 19.79, 21.48, 22.59, 23.34, 24.38, 24.83, 25.41, 25.82, 26.35, 26.91, 27.71, 28.26, 28.72, 29.15, 30.29, 31.16, 35.10, 36.12. In one embodiment, the PXRD pattern of needle-type crystals is substantially the same as the PXRD pattern of FIG. 3.

The invention is also directed to needle-shaped cefsulodin sodium crystals.

The invention is also directed to spherical-shaped cefsulodin sodium crystals.

Needle-shaped crystals are more stable than spherical-shaped crystals.

Without further elaboration, it is believed that one skilled in the art using the preceding description can utilize the invention to the fullest extent. The following examples are illustrative only, and not limiting of the disclosure in any way whatsoever.

EXAMPLES

Example 1

Recrystallization of Cefsulodin from Dimethylformamide

Provided below is a method for recrystallizing cefsulodin from dimethylformamide (DMF).

1. 10.0 g of cefsulodin powder was weighed into a 500 mL flask. The cefsulodin free acid powder was maintained in a freezer and was allowed to warm to room temperature before being used.

2. 25 mL of DMF was added to the flask with vigorous stirring to provide a clear solution at room temperature 3. Stirring was stopped, the solution cooled, and then stored at 4° C. overnight to provide cefsulodin crystals. The crystals of cefsulodin were collected by vacuum filtration. The crystals were washed with water (2×30 mL), ethanol (2×30 mL), and diethyl ether (30 mL).

4. The crystal were then dried under higher vacuum over $P_2O_5$.

5. The purity of the final product was determined using HPLC.

6. The yield was 80-85%.

Example 2

Conversion of Cefsulodin to the Mono Sodium Salt

Cefsulodin sodium was prepared from cefsulodin by the following process:

1. 30.0 g (56.1 mmol) of cefsulodin powder was weighed into a 500 mL flask. The cefsulodin powder was maintained in a freezer and was allowed to warm to room temperature before being used.
2. 175 mL of ethanol was added to the flask with vigorous stirring to provide a suspension at room temperature.
3. To the suspension, with stirring, was added 120 mL of deionized water (DI water) to provide a clear solution.
4. 5.064 g (61.36 mmol) of anhydrous sodium acetate was weighed into a 250 mL flask and 180 mL of water was added to the flask to provide a clear solution. The solution was cooled to 0-5° C.
5. Using an addition funnel and with vigorous stirring, while monitoring the pH, the sodium acetate solution was slowly added drop wise to the cefsulodin solution (rapid addition can result in the formation of an undesirable co-precipitate).
6. The addition of sodium acetate was continued until the final pH was between about 4.0-4.25. About 165 mL of the sodium acetate solution was required to reach a pH of 4.2. (Too high a pH is indicative of di-sodium salt formation and too low pH indicates that the acid form is still present).
7. The neutralized cefsulodin solution was filtered through Buchner filter funnel.
8. Using an addition funnel and with vigorous stirring (250 rpm), 450 mL of ethanol was added to the clear, filtered, neutralized cefsulodin solution. Crystallization started when the addition of ethanol was nearly complete (adding ethanol too rapidly and/or cooling the solution can result in the formation of an undesirable co-precipitate).
9. The reaction mixture was allowed to sit untouched for about 4 hours to allow the crystallization to complete.
10. The cefsulodin mono sodium salt was collected by vacuum filtration and the filter cake was washed with ethanol (2×30 mL) and diethyl ether (30 mL).
11. The filtered material was dried under high vacuum over $P_2O_5$ until the water content was between 3-3.6%. The material was ground periodically while drying. A highly granular texture or lumps suggests that water may be entrapped in the material. As discussed herein, higher water content compromises the stability of the final product.
12. The purity of the final product was determined using HPLC. Typically, the purity of the cefsulodin sodium obtained by the above-identified process is above 98%.
13. A second crop of crystals may be obtained from the mother liquor by storing the mother liquor overnight at 4° C.
14. The shape of the crystals was confirmed by microscopy. The crystals were needle-shaped crystals.
15. The yield was 80-85%. The material should be protected from exposure to light, heat, and moisture. The product is stored at −20° C.

Example 3

Influence of Water Content on the Stability of the Cefsulodin Sodium

Three lots of cefsulodin sodium, prepared according to the process described in Example 2, were stored at 55° C. and 40° C. and the purity of the sample determined as a function of time using HPLC. The lots had a water content of 3.1%, 3.6%, and 3.2%. The stability of a lyophilized sample of cefsulodin sodium containing about 5-6% water at 55° C. was also determined. The lyophilized sample was prepared by suspending cefsulodin in water, adding sodium hydroxide until the cefsulodin dissolved, and then removing the water by lyophilization. The area of the HPLC peak corresponding to cefsulodin was used to determine purity. The following assay was used to determine purity:

Buffers and Solvents:
1. 25 mM Sodium Acetate pH 4.5
  a. Measure out 2 L of HPLC grade water.
  b. Add 4.1 g of sodium acetate.
  c. Mix until dissolved.
  d. Adjust the pH to 4.5 with HPLC grade acetic acid.
  e. Filter the solution through a nylon filter.
2. 3% acetonitrile-97% 25 mM sodium acetate pH 4.5 (Mobile Phase A)
  a. Measure out 1940 mL of 25 mM sodium acetate into a 2 L flask.
  b. Add 60 mL of HPLC grade acetonitrile.
  c. Mix well.
3. HPLC Grade acetonitrile (Mobile Phase B)
  a. Transfer acetonitrile into a 1 L flask.

Sample Preparation:
1. Weigh out about 10 mg of cefsulodin into a 15 mL conical tube.
2. Add an equal volume of mobile phase A and mix to dissolve (1 mg/mL cefsulodin Stock solution).
3. Transfer 1 mL of cefsulodin stock solution into another 15 mL conical tube.
4. Add 7 mL of mobile phase A to make a 0.125 mg/mL solution of cefsulodin.
5. Filter this solution through a nylon syringe filter into an HPLC vial.
6. Analyze the sample by HPLC using the conditions described below.

HPLC Method
Column: Phenomenex Luna 5 um C18(2) 100 A, 50×3.00 mm
Solvents: Pump A-Mobile Phase A
Pump B-Mobile Phase B
Flow Rate: 1 mL/min
Detection wavelength: 254 nm
Temperature: Ambient
Run Time: 8 min
Initial Conditions: 100% Pump A-0% Pump B
Gradient: Beckman System

| Time (min) | Module | Function | Value | Duration (min) |
|---|---|---|---|---|
| 0.3 | Pump | % B | 70.00 | 2.50 |
| 3.50 | Pump | % B | 0.00 | 0.50 |
| 8.00 | Detector | Stop Data | | |

The above gradient can be summarized as follows: maintain at 0% B for 0.3 min; at 0.3 min run a gradient to 70% B for 2.5 min; maintain at 70% B for 1 min; at 3.5 min go back to 0% B for 0.5 min; run at 0% B until the 8.00 min mark.

The results of the stability study are provided in the following tables:

Stability at 55° C.

| | Purity | | | | | |
|---|---|---|---|---|---|---|
| Sample | Day 0 | Day 7 | Day 14 | Day 21 | Day 28 | Day 35 |
| Lot 1 (3.1% water) | 99.2% | 97.2% | 96.0% | 94.9% | 94.3% | 93.4% |
| Lot 2 (3.6% water) | 99.2% | 97.1% | 96.1% | 94.7% | 94.4% | 92.9% |
| Lot 3 (3.2% water) | 99.3% | 96.9% | 96.1% | 94.8% | 93.9% | — |
| Lyophilized (5-6% water) | 98.8% | | | | 80.4% | |

| | Purity | | | | |
|---|---|---|---|---|---|
| Sample | Day 42 | Day 49 | Day 56 | Day 63 | Day 70 |
| Lot 1 (3.1% water) | 91.8% | 90.9% | 90.5% | 89.8% | 89.1% |
| Lot 2 (3.6% water) | 91.8% | 91.0% | 90.1% | 89.8% | 89.2% |
| Lot 3 (3.2% water) | 93.4% | 92.6% | 92.7% | 91.3% | 91.3% |
| Lyophilized (5-6% water) | | | | | |

Stability at 40° C.

| | Purity | | | | | |
|---|---|---|---|---|---|---|
| Sample | Day 0 | Day 7 | Day 14 | Day 21 | Day 28 | Day 35 |
| Lot 1 (3.1% water) | 99.2% | 98.2% | 98.2% | 97.5% | 97.2% | 96.4% |
| Lot 2 (3.6% water) | 99.2% | 98.5% | 98.3% | 97.7% | 97.1% | 96.8% |
| Lot 3 (3.2% water) | 99.3% | 98.4% | 98.5% | 98.1% | 97.9% | — |

| | Purity | | | | |
|---|---|---|---|---|---|
| Sample | Day 42 | Day 49 | Day 56 | Day 63 | Day 70 |
| Lot 1 (3.1% water) | 96.3% | 96.4% | 96.0% | 96.0% | 95.3% |
| Lot 2 (3.6% water) | 96.5% | 96.4% | 96.4% | 96.1% | 95.6% |
| Lot 3 (3.2% water) | 96.2% | 97.2% | 97.3% | 97.0% | 97.0% |

The results of the stability study show that cefsulodin sodium prepared by the process of the invention containing water in an amount ranging from about 3% to about 4% by weight is more stable than cefsulodin sodium prepared by a typical manufacturing process and then removing the water by lyophilization to provide cefsulodin sodium with a water content of about 5-6% by weight. It is believed that cefsulodin sodium giving a water content less than 2% is also less stable.

The PXRD pattern of FIG. 3 corresponds to cefsulodin sodium Lot 1. The following parameters were used to determine the PXRD pattern Rigaku Ultima-III Theta:Theta diffractometer
Radiation: Cu K-alpha
Power: 40 kV, 44 mA
Bragg-Brentano parafocusing optics
Optics:
2.5 deg incident beam Soller slit
12 mm height limiting slit (beam mask)
Variable divergence slit (0-10 mm)
2.5 deg diffracted beam Soller slit
Variable scatter slit (0-20 mm)
0.6 mm receiving slit
beta filter
Scintillation detector Scans were from 2-65 degrees 2-Theta with a scan speed of 3.6 deg/min and a step size of 0.03 degrees 2-Theta.

Example 4

Conversion of Cefsulodin to the Mono Sodium Salt-Spherical-Type Crystals

Cefsulodin (5.0762 g) was dissolved in 10 mL of DMF and cooled in an ice bath. To this cold, yellow, syrupy solution was added 1.1 eq. of sodium acetate in 15 mL of water with stirring. The mixture was stirred at ice temperature for 10 more minutes. The mixture was then placed in a refrigerator overnight. The crystallized cefsulodin sodium was filtered, dried using heat under reduced pressure to a water content of about 3.18% by weight. 2.82 g of cefsulodin sodium were obtained (63%). Microscopic analysis of the resulting crystals showed that the cefsulodin sodium was spherical-type crystals.

Example 5

Stability of Needle-Shaped Cefsulodin Sodium Crystals and Spherical-Shaped Cefsulodin Sodium Crystals Needle-shaped cefsulodin sodium crystals were obtain according to a process similar to the process described in Example 2. The crystals had a water content of about 3.23% by weight.

Spherical-shaped cefsulodin sodium crystals were obtain according to the process described in Example 3. The crystals had a water content of about 3.18% by weight.

The stability of each crystal form was measured at 55° C.

| | Purity | | | |
|---|---|---|---|---|
| Crystal Form | Day 1 | Day 7 | Day 14 | Day 21 |
| Spherical-shaped | 98.5 | 86.3 | 83.7 | 83.1 |
| Needle-shaped | 99.2 | 98.1 | 96.8 | 95.7 |

The results of the stability study show that the needle-shaped crystals are more stable than the spherical-shaped crystals.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. A process for making cefsulodin sodium comprising:
   (i) dissolving cefsulodin in a solvent comprising an organic solvent to provide a solution of cefsulodin,
   (ii) adding about 1 equivalent of a sodium salt of a base to the solution of cefsulodin to provide a solution of cefsulodin sodium, and
   (iii) separating the cefsulodin sodium from the solution of cefsulodin sodium.

2. The process of claim 1, wherein the solvent comprising an organic solvent is dimethylformamide substantially free of another organic solvent.

3. The process of claim 2, wherein the solvent comprising an organic solvent is a mixture of dimethylformamide and water.

4. The process of claim 1, wherein the solvent comprising an organic solvent further comprises water.

5. The process of claim 1, wherein the sodium salt of a base is a sodium salt of a carboxylate anion.

6. The process of claim 5, wherein the sodium salt of a base is sodium acetate.

7. The process of claim 1, wherein a solution of the sodium salt of a base is added to the solution of cefsulodin.

8. The process of claim 7, wherein the solution of the sodium salt of a base is an aqueous solution.

9. The process of claim 6, wherein a solution of sodium acetate is added to the solution of cefsulodin.

10. The process of claim 9, wherein the solution of sodium acetate is an aqueous solution.

11. The process of claim 1, wherein the cefsulodin sodium is separated from the solution of cefsulodin sodium by adding an anti-solvent to the solution of cefsulodin sodium to precipitate the cefsulodin sodium.

12. The process of claim 11, wherein the solvent comprising an organic solvent is dimethylformamide or a mixture of dimethylformamide and water and the anti-solvent is water.

13. A process for making cefsulodin sodium comprising:
    (i) dissolving cefsulodin in dimethylformamide or a mixture of dimethylformamide and water to provide a solution of cefsulodin,
    (ii) adding about 1 equivalent of a sodium salt of a base to the solution of cefsulodin to provide a solution of cefsulodin sodium, and
    (iii) separating the cefsulodin sodium from the solution of cefsulodin sodium.

14. The process of claim 13, wherein the sodium salt of a base is a sodium salt of a carboxylate anion.

15. The process of claim 14, wherein the sodium salt of a carboxylate anion is sodium acetate.

16. The process of claim 15, wherein a solution of sodium acetate is added to the solution of cefsulodin.

17. The process of claim 13, wherein a solution of the sodium salt of a base is added to the solution of cefsulodin.

18. The process of claim 13, wherein the cefsulodin sodium is separated from the solution of cefsulodin sodium by adding an anti-solvent to the solution of cefsulodin sodium to precipitate the cefsulodin sodium.

19. The process of claim 18, wherein the anti-solvent is water.

20. The process of claim 1, further comprising drying the cefsulodin to a water content ranging from about 2.5 to 4.5% by weight.

21. The process of claim 9, further comprising drying the cefsulodin sodium to a water content ranging from about 2.5 to 4.5% by weight.

22. A process for making cefsulodin sodium comprising:
    (i) dissolving cefsulodin in ethanol or a mixture of ethanol and water to provide a solution of cefsulodin,
    (ii) adding about 1 equivalent of a sodium salt of a base to the solution of cefsulodin to provide a solution of cefsulodin sodium, and
    (iii) separating the cefsulodin sodium from the solution of cefsulodin sodium.

23. The process of claim 22, wherein the sodium salt of a base is a sodium salt of a carboxylate anion.

24. The process of claim 23, wherein the sodium salt of a carboxylate anion is sodium acetate.

25. The process of claim 24, wherein a solution of sodium acetate is added to the solution of cefsulodin.

26. The process of claim 22, wherein a solution of the sodium salt of a base is added to the solution of cefsulodin.

27. The process of claim 22, wherein the cefsulodin sodium is separated from the solution of cefsulodin by adding an anti-solvent to the solution of cefsulodin to precipitate the cefsulodin sodium.

28. The process of claim 27, wherein the anti-solvent is ethanol.

29. The process of claim 13, wherein the cefsulodin is dissolved in dimethylformamide substantially free of another organic solvent.

30. The process of claim 13, wherein the cefsulodin is dissolved in a mixture of dimethylfoimamide and water.

31. The process of claim 16, wherein the solution of sodium acetate is an aqueous solution.

32. The process of claim 17, wherein the solution of the sodium salt of a base is an aqueous solution.

33. The process of claim 25, wherein the solution of sodium acetate is an aqueous solution.

34. The process of claim 26, wherein the solution of the sodium salt of a base is an aqueous solution.

35. The process of claim 13, further comprising drying the cefsulodin sodium to a water content ranging from about 2.5 to 4.5% by weight.

36. The process of claim 16, further comprising drying the cefsulodin sodium to a water content ranging from about 2.5 to 4.5% by weight.

37. The process of claim 22, further comprising drying the cefsulodin sodium to a water content ranging from about 2.5 to 4.5% by weight.

38. The process of claim 25, further comprising drying the cefsulodin sodium to a water content ranging from about 2.5 to 4.5% by weight.

39. The process of claim 1, wherein the cefsulodin is cefsulodin that has been crystallized from dimethyl formamide.

40. The process of claim 13, wherein the cefsulodin is cefsulodin that has been crystallized from dimethyl formamide.

41. The process of claim 22, wherein the cefsulodin is cefsulodin that has been crystallized from dimethyl formamide.

* * * * *